United States Patent
Le et al.

(10) Patent No.: US 7,608,063 B2
(45) Date of Patent: Oct. 27, 2009

(54) DUAL LUMEN ASPIRATION CATHETER SYSTEM

(75) Inventors: Hieu V. Le, Brooklyn Park, MN (US); Michael P. Schrom, Wyoming Township, MN (US); Diana L. Dutcher, Maple Grove, MN (US); Kyle R. Matson, Plymouth, MN (US); Dean A. Swanson, Forest Lake, MN (US); Kathleen C. Grant, Rogers, MN (US); James T. Klee, Maple Grove, MN (US)

(73) Assignee: MEDRAD, Inc., Indianola, PA (US)

( * ) Notice: Subject to any disclaimer, the term of this patent is extended or adjusted under 35 U.S.C. 154(b) by 64 days.

(21) Appl. No.: 11/360,148

(22) Filed: Feb. 23, 2006

(65) Prior Publication Data

US 2007/0197956 A1    Aug. 23, 2007

(51) Int. Cl.
    *A61M 25/00* (2006.01)
(52) U.S. Cl. .......................... 604/264; 604/43
(58) Field of Classification Search .............. 604/43, 604/264, 523, 524–529, 35, 39, 44
    See application file for complete search history.

(56) References Cited

U.S. PATENT DOCUMENTS

| | | | |
|---|---|---|---|
| 2,564,809 A | 8/1951 | Levene | |
| 3,625,793 A | 12/1971 | Sheridan | |
| 3,965,901 A | 6/1976 | Penny et al. | |
| 4,202,332 A | 5/1980 | Tersteegen | |
| 4,300,550 A | 11/1981 | Gandi et al. | |
| 4,385,631 A | 5/1983 | Uthmann | |
| 4,468,216 A | 8/1984 | Muto | |
| 4,568,329 A | 2/1986 | Mahurkar | |
| 4,589,412 A * | 5/1986 | Kensey ...................... 606/159 | |
| 4,692,141 A | 9/1987 | Mahurkar | |
| 4,782,834 A * | 11/1988 | Maguire et al. ............. 606/194 | |
| 4,808,155 A | 2/1989 | Mahurkar | |
| 4,928,693 A | 5/1990 | Goodin et al. | |
| 4,932,413 A | 6/1990 | Shockey et al. | |
| 5,040,548 A | 8/1991 | Yock | |
| 5,084,013 A | 1/1992 | Takase | |

(Continued)

OTHER PUBLICATIONS

International Search Report issued Oct. 16, 2008 in corresponding PCT Application PCT/US07/04523.

*Primary Examiner*—Nicholas D Lucchesi
*Assistant Examiner*—Aarti Bhatia
(74) *Attorney, Agent, or Firm*—David Schramm (57) ABSTRACT

A dual lumen aspiration catheter system with an aspiration catheter, a hub and a flexible strain relief, and a suction assembly. The aspiration catheter includes multiple successively connected flexible tubular components each increasing in relative flexibility in the distal direction, the most proximal tubular component connectingly extending from the hub and through the flexible strain relief. The tubular components of the aspiration catheter include, in order proximally to distally, a composite tube, an intermediate tube, a dual lumen tube, and a flexible tip tube. The dual lumen tube includes eccentrically co-located large and small tubular portions forming eccentrically co-located large and small lumens to provide a minimum cross section. The distal end of the dual lumen tube includes a convex beveled edge. The convex beveled edge and the flexible tip tube singly or jointly inflict minimal traumatic contact with a vessel wall when urged along a tortuous vascular path.

11 Claims, 12 Drawing Sheets

U.S. PATENT DOCUMENTS

| | | | |
|---|---|---|---|
| 5,163,905 A * | 11/1992 | Don Michael | 604/101.03 |
| 5,180,367 A | 1/1993 | Kontos et al. | |
| 5,195,955 A * | 3/1993 | Don Michael | 604/22 |
| 5,195,978 A | 3/1993 | Schiffer | |
| 5,221,256 A * | 6/1993 | Mahurkar | 604/43 |
| 5,273,527 A | 12/1993 | Schatz et al. | |
| 5,290,241 A | 3/1994 | Kraus et al. | |
| 5,300,085 A | 4/1994 | Yock | |
| 5,306,261 A | 4/1994 | Alliger et al. | |
| 5,318,518 A | 6/1994 | Plechinger et al. | |
| 5,370,609 A * | 12/1994 | Drasler et al. | 604/22 |
| 5,443,457 A | 8/1995 | Ginn et al. | |
| 5,476,450 A | 12/1995 | Ruggio | |
| 5,549,553 A | 8/1996 | Ressemann et al. | |
| 5,718,683 A | 2/1998 | Ressemann et al. | |
| 5,769,868 A | 6/1998 | Yock | |
| 5,827,229 A | 10/1998 | Auth et al. | |
| 5,938,645 A | 8/1999 | Gordon | |
| 6,152,909 A * | 11/2000 | Bagaoisan et al. | 604/523 |
| 6,159,195 A * | 12/2000 | Ha et al. | 604/500 |
| 6,165,163 A | 12/2000 | Chien et al. | |
| 6,540,734 B1 | 4/2003 | Chiu et al. | |
| 6,821,287 B1 | 11/2004 | Jang | |
| 6,827,701 B2 | 12/2004 | MacMahon et al. | |
| 6,849,068 B1 | 2/2005 | Bagaoisan et al. | |
| 6,921,396 B1 | 7/2005 | Wilson et al. | |
| 7,294,117 B2 | 11/2007 | Provost-tine et al. | |
| 7,297,134 B2 | 11/2007 | Krivoruchko | |
| 2002/0082525 A1 | 6/2002 | Oslund et al. | |
| 2002/0091372 A1 | 7/2002 | Cragg et al. | |
| 2004/0049225 A1 | 3/2004 | Denison | |
| 2004/0220515 A1 | 11/2004 | Constantz | |
| 2005/0027236 A1 | 2/2005 | Douk | |
| 2005/0107819 A1 | 5/2005 | Sater | |
| 2005/0240165 A1 | 10/2005 | Miki et al. | |
| 2005/0245866 A1 | 11/2005 | Azizi | |
| 2005/0277976 A1 | 12/2005 | Galdonik et al. | |

* cited by examiner

DUAL LUMEN ASPIRATION CATHETER SYSTEM

CROSS REFERENCES TO RELATED APPLICATIONS

None.

BACKGROUND OF THE INVENTION

1. Field of the Invention

The present invention relates to the field of catheters, and more directly relates to an aspiration catheter system having a dual lumen tube, wherein a small lumen is co-located eccentric to and within a large lumen, and wherein a convex beveled edge and a flexible tip tube are located at the distal end of the dual lumen tube.

2. Description of the Prior Art

Prior art systems or devices have provided aspiration catheters incorporating more than one lumen. Generally, the location of a small lumen, usually used for passage over a guidewire, was attachingly located exteriorly to a large lumen. Such an arrangement added to the overall cross sectional profile of the catheter device, thereby restricting passage of the device along smaller sized blood vessels. Additional material, incorporated to form adjacent large and small lumen one-piece extrusions, added to the bulk of the device, thereby detrimentally limiting the flexibility of the aspiration catheter, especially at the distal tip portion.

Other systems incorporated tubular sections having the same flexibility along the length, thereby limiting the flexibility within a tortuous path. Often, the shape at the distal portion of a dual lumen catheter was not conducive to easy and minimum trauma passage along a blood vessel or vein and often abrasive passage occurred. The present invention overcomes the difficulties encountered by the use of prior art aspiration catheters or aspiration catheter systems.

SUMMARY OF THE INVENTION

The general purpose of the present invention is to provide a dual lumen aspiration catheter system.

According to one embodiment of the present invention, there is provided a dual lumen aspiration catheter system including a hub and a flexible strain relief, an aspiration catheter, and a suction assembly which attaches to and is in communication with the aspiration catheter. The aspiration catheter includes multiple successively connected flexible tubular components each increasing in relative flexibility in the distal direction, the most proximal tubular component connectingly extending from the hub and through the flexible strain relief. The tubular components of the aspiration catheter include, in order proximally to distally, a composite tube, an intermediate tube, a dual lumen tube, and a flexible tip tube, each tubular component having one or more lumens associated therewith. The dual lumen tube includes a large radius tubular portion and a small radius tubular portion being eccentrically co-located to delineate a large lumen and a small lumen, respectively, where the small lumen is eccentric to and located substantially within the general profile of the large lumen. The dual lumen tube includes a distal end having a convex beveled edge. The convex beveled edge and the flexible tip tube singly or in combination facilitate ease of passage of the aspiration catheter along a tortuous path of a blood vessel, vein or the like. The flexible tip tube secures to the small radius tubular portion of the dual lumen tube at a position adjacent to and partially encompassed by the convex beveled edge to communicate with the small lumen. The small lumen includes a proximally located exit end. The flexible tip tube and the small lumen form a path for accommodation of a guidewire, whereby a guidewire can enter the flexible tip tube lumen at the distal end and exit the small lumen at the proximally located exit end. The large lumen of the large radius tubular portion is used to evacuate loose material from a blood vessel, vein or the like in cooperation with the suction assembly. A fluoroscopic ring or marker band is located about the distal end of the small radius tubular portion. The suction assembly includes a syringe, a stopcock, an extension tube, and connectors to provide for a low pressure source for evacuation of debris, thrombi, emboli and the like through the hub and aspiration catheter.

One significant aspect and feature of the present invention is a dual lumen aspiration catheter system having a suction assembly, a hub and strain relief, and an aspiration catheter.

Another significant aspect and feature of the present invention is an aspiration catheter which is increasingly flexible along portions of the length thereof from the proximal end to the distal end.

Yet another significant aspect and feature of the present invention is the use of an aspiration catheter having a large radius tubular portion and an intersecting small radius tubular portion commonly and eccentrically co-located, thereby delineating a large lumen and a small lumen.

Still another significant aspect and feature of the present invention is the use of an aspiration catheter having large and small lumens commonly and eccentrically co-located, wherein the small lumen is eccentric to and located substantially within the general profile of the large lumen.

A further significant aspect and feature of the present invention is the use of eccentrically co-located large and small tubular portions to provide a minimum cross section aspiration catheter.

Another further significant aspect and feature of the present invention is a dual lumen tube having a convex beveled edge distal tip conducive to easy and minimum trauma passage along a tortuous path blood vessel or vein.

Another further significant aspect and feature of the present invention is the use of a flexible tip tube secured over and about a small radius tubular portion at the distal portion of a dual lumen tube at a position adjacent to and partially encompassed by a convex beveled edge to communicate with the small lumen of a small radius tubular portion.

Another further significant aspect and feature of the present invention is the use of a small radius tubular portion and connected flexible tip tube for accommodation and passage of a guidewire.

Another further significant aspect and feature of the present invention is the use of a proximal flared section of dual lumen tube to accommodate the distal end of an intermediate tube.

Having thus briefly described an embodiment of the present invention and having mentioned some significant aspects and features of the present invention, it is the principal object of the present invention to provide a dual lumen aspiration catheter system.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 12 shows a blood vessel having a tortuous path and the flexible tip tube and the convex beveled edge at the distal portion of the dual lumen tube at the site of excess debris, thrombi, emboli and the like.

DETAILED DESCRIPTION OF THE PREFERRED EMBODIMENT

Figure 1:
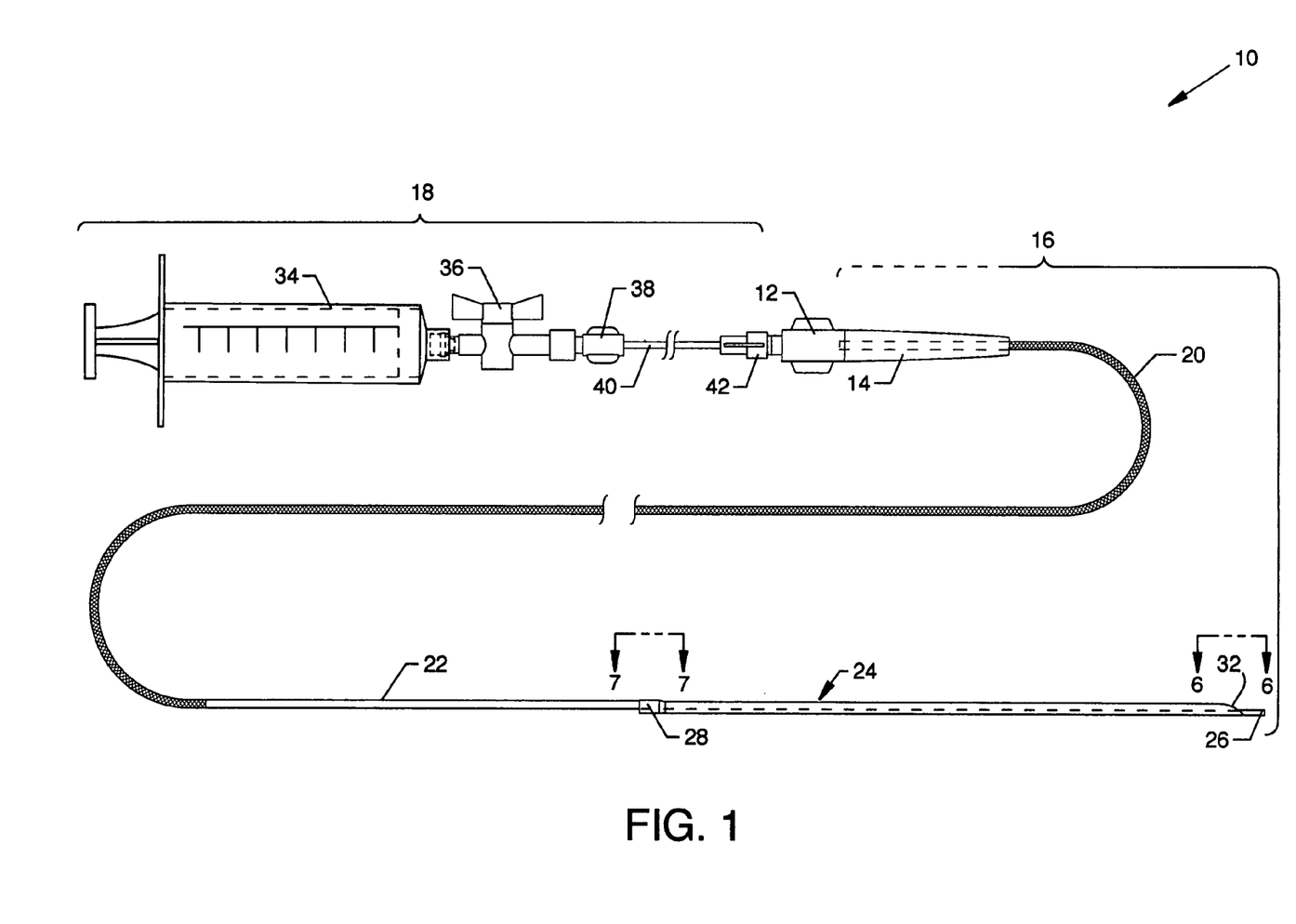
FIG. 1 is a plan view of a dual lumen aspiration catheter system, the present invention.

FIG. 1 is a plan view of a dual lumen aspiration catheter system 10, the present invention, including a hub 12, a strain relief 14, an aspiration catheter 16, and a suction assembly 18. The aspiration catheter 16 is comprised of a composite tube 20, an intermediate tube 22 of a thermoplastic such as Pebax or other suitable material, a flexible dual lumen tube 24 preferably of a thermoplastic such as Pebax or other suitable flexible material, and a flexible tip tube 26. The proximal end of the composite tube 20 extends through the strain relief 14 and secures to the hub 12, and the distal end of the composite tube 20 connects to and suitably communicates with the proximal end of the intermediate tube 22. The composite tube 20 can be made of polyimide layers with stainless steel flat braid wires in between the layers and is designed to have a thin wall or largest lumen to maximize the evacuation power of an evacuation syringe. The composite tube 20 incorporates braided construction for strength and torqueability, but can be effectively formed in other ways, for example, by using reinforcing components such as fibers, wound strands, rings, wraps or combinations thereof. The proximal end of the dual lumen tube 24 includes a flared section 28 for the accommodation of the distal end of the intermediate tube 22. The distal portion of the dual lumen tube 24 includes a distal end which connects to and partially communicates with the flexible tip tube 26. The distal portion of the dual lumen tube 24 also includes a convex beveled edge 32. The suction assembly 18, which provides a low pressure for evacuation of debris, thrombi, emboli and the like through the aspiration catheter 16, includes a syringe 34 which can be lockable, a stopcock 36 connected to one end of the syringe 34, a connector 38 connecting one end of an extension tube 40 to the stopcock 36, and a connector 42 connecting one end of the extension tube 40 to the proximal end of the hub 12.

Different stiffness and flexibilities are incorporated into the design of the aspiration catheter 16, wherein the components become more flexible in a distal direction. For purpose of example and illustration, the composite tube 20 can be 80-120 centimeters in length and is the stiffest component of the aspiration catheter 16. The intermediate tube 22 can be in a range of 15-25 centimeters in length and can be comprised of 72 durometer Pebax and is more flexible than the composite tube 20. The dual lumen tube 24 can be 25 centimeters in length and can be comprised of 63 durometer Pebax and is more flexible than the intermediate tube 22. The flexible tip tube 26 can be of a softer 25-55 durometer Pebax, wherein trauma is reduced when accessing the target lesion.

Figure 2:
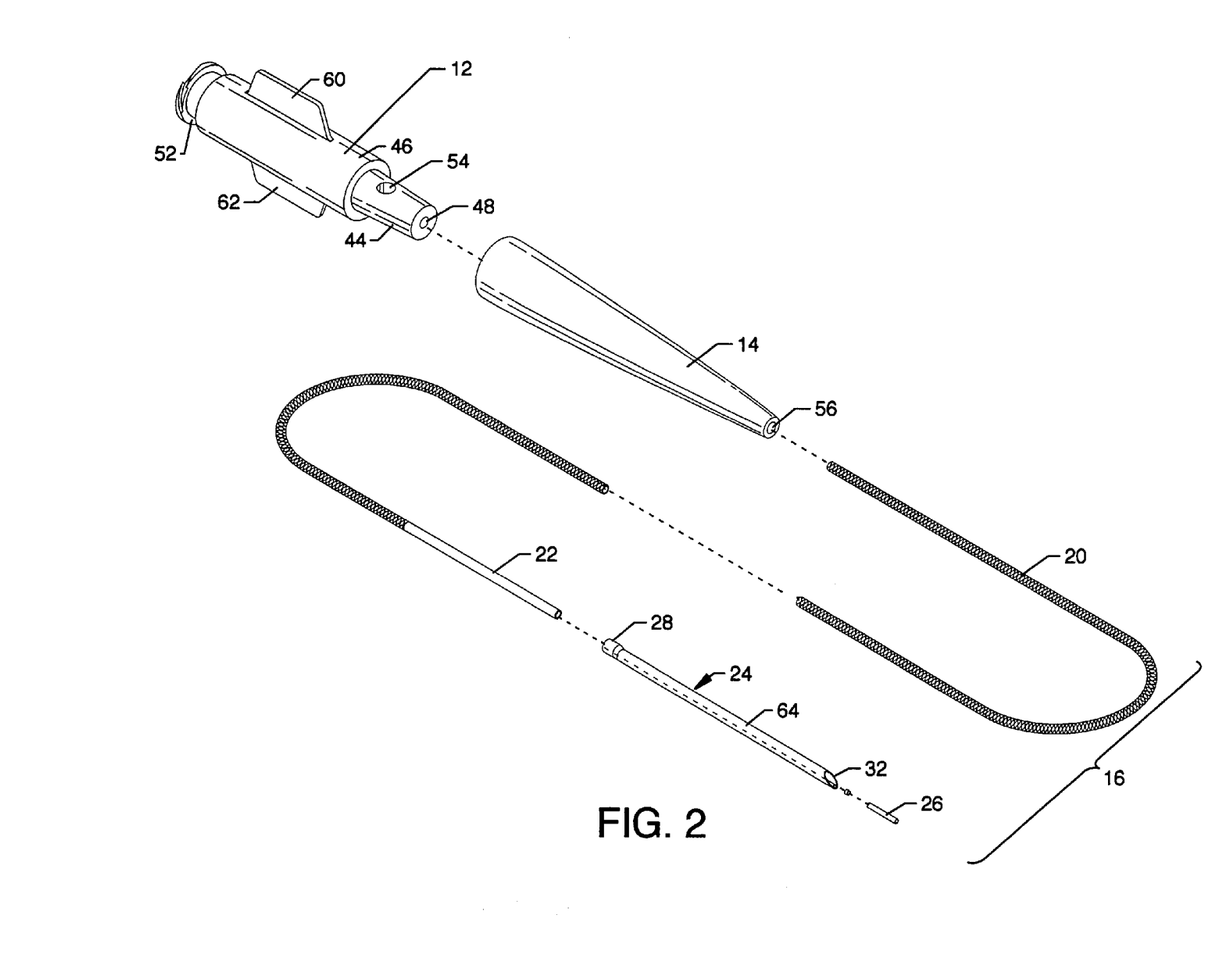
FIG. 2 is an exploded isometric view of the aspiration catheter, the hub, and the strain relief of the dual lumen aspiration catheter system.
Figure 3:
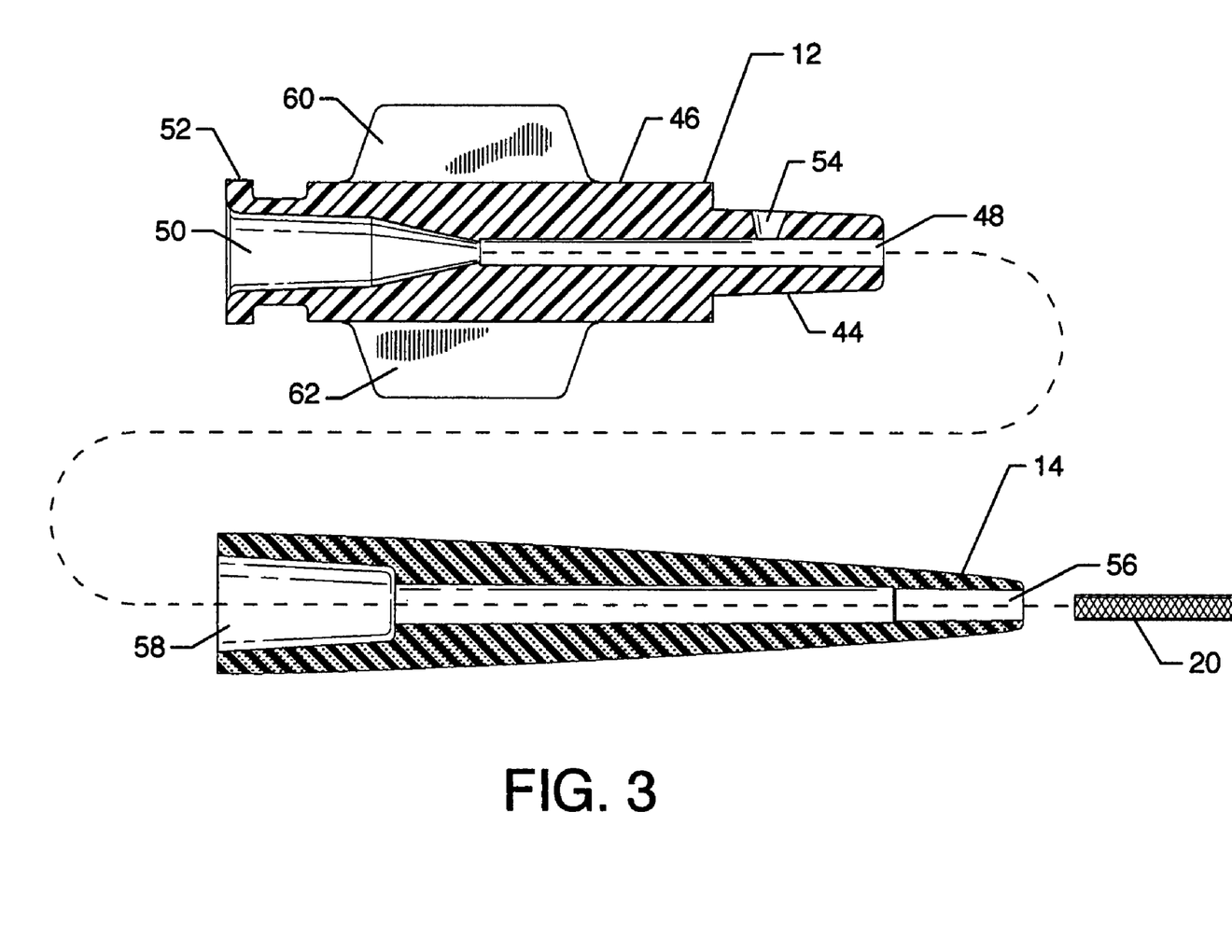
FIG. 3 is an exploded cross section view of the hub and the strain relief of the dual lumen aspiration catheter system.
Figure 4:
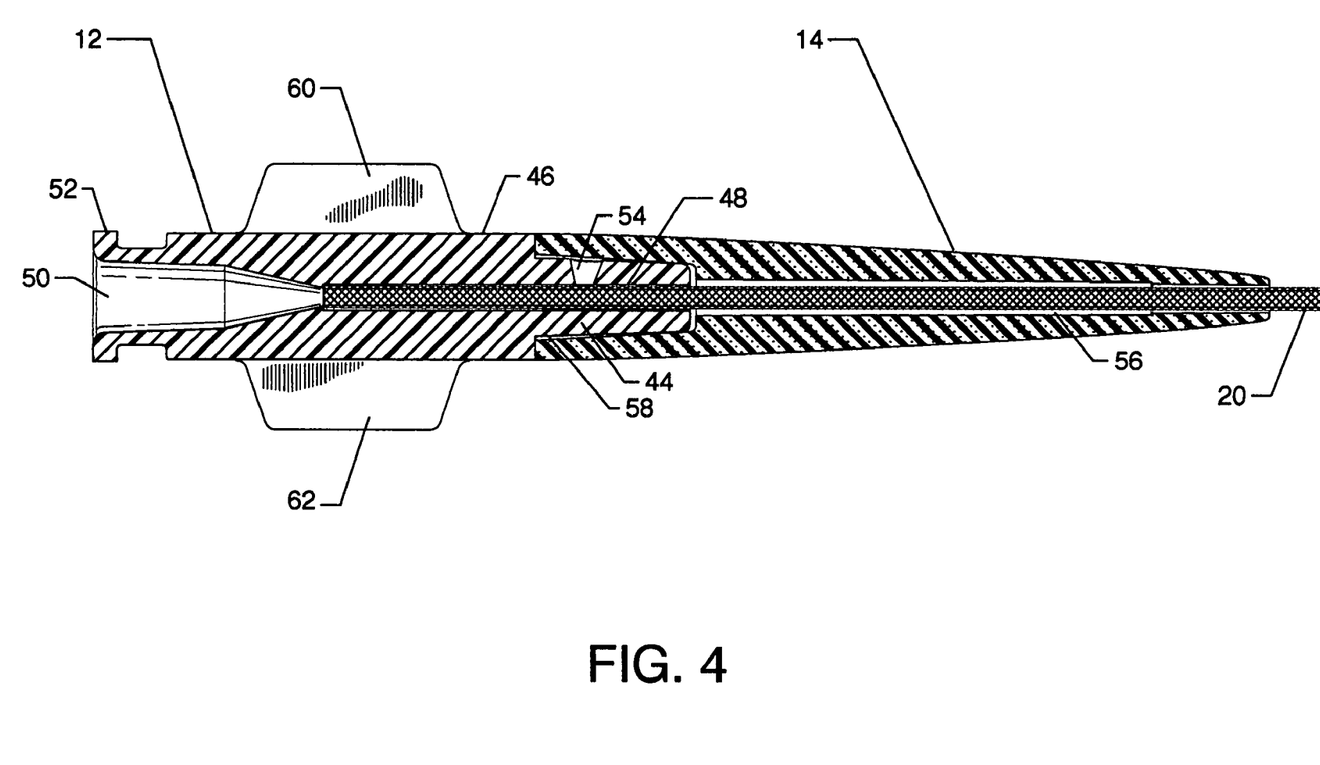
FIG. 4 is an assembled cross section view of the hub and the strain relief of the dual lumen aspiration catheter system.

FIG. 2 is an exploded isometric view of the aspiration catheter 16, the hub 12, and the strain relief 14 of the dual lumen aspiration catheter system 10; and FIG. 3 is an exploded cross section view of the hub 12 and the strain relief 14 of the dual lumen aspiration catheter system 10. The hub 12 and the strain relief 14, shown in FIGS. 2 and 3, are now described. The hub 12 is generally cylindrical in shape, fashioned preferably of plastic or other suitable material, and includes a tapered extension 44 extending from a main body 46. A lumen 48 extends along the centerline of the hub 12 through the tapered extension 44 and through the main body 46 to intersect and communicate with a cavity 50, which can be tapered, at the opposite end of the hub 12 where the cavity 50 also extends along the centerline of the hub 12. A connection flange 52 is located at one end of the main body 46 of the hub 12. An orifice 54 extends through the tapered extension 44 to intersect the lumen 48 of the hub 12 in order to provide a path for passage and/or for inclusion of adhesive therethrough and/or therein to contact and secure the proximal end of the composite tube 20, which also extends through a lumen 56 of the strain relief 14, to and partially within the lumen 48 of the hub 12, as shown in FIG. 4. The strain relief 14 comprised of a flexible plastic or other suitable material includes the lumen 56 extending along the centerline of the strain relief 14 to intersect a tapered extension receptor 58 also extending along the centerline of the strain relief 14. The shape of the tapered extension receptor 58 is complementary to the shape of the tapered extension 44 of the hub 12 to ensure a proper mutual fit, as shown in FIG. 4. An adhesive or other suitable method of affixing the tapered extension 44 of the hub 12 within the tapered extension receptor 58 can be used. Grasping tabs 60 and 62 extend outwardly from the periphery of the hub main body 46 to assist in maneuvering of the aspiration catheter 16.

FIG. 4 is an assembled cross section view of the hub 12 and the strain relief 14 of the dual lumen aspiration catheter system 10. Shown in particular is the relationship of the composite tube 20 to the assembled hub 12 and strain relief 14.

Figure 5:
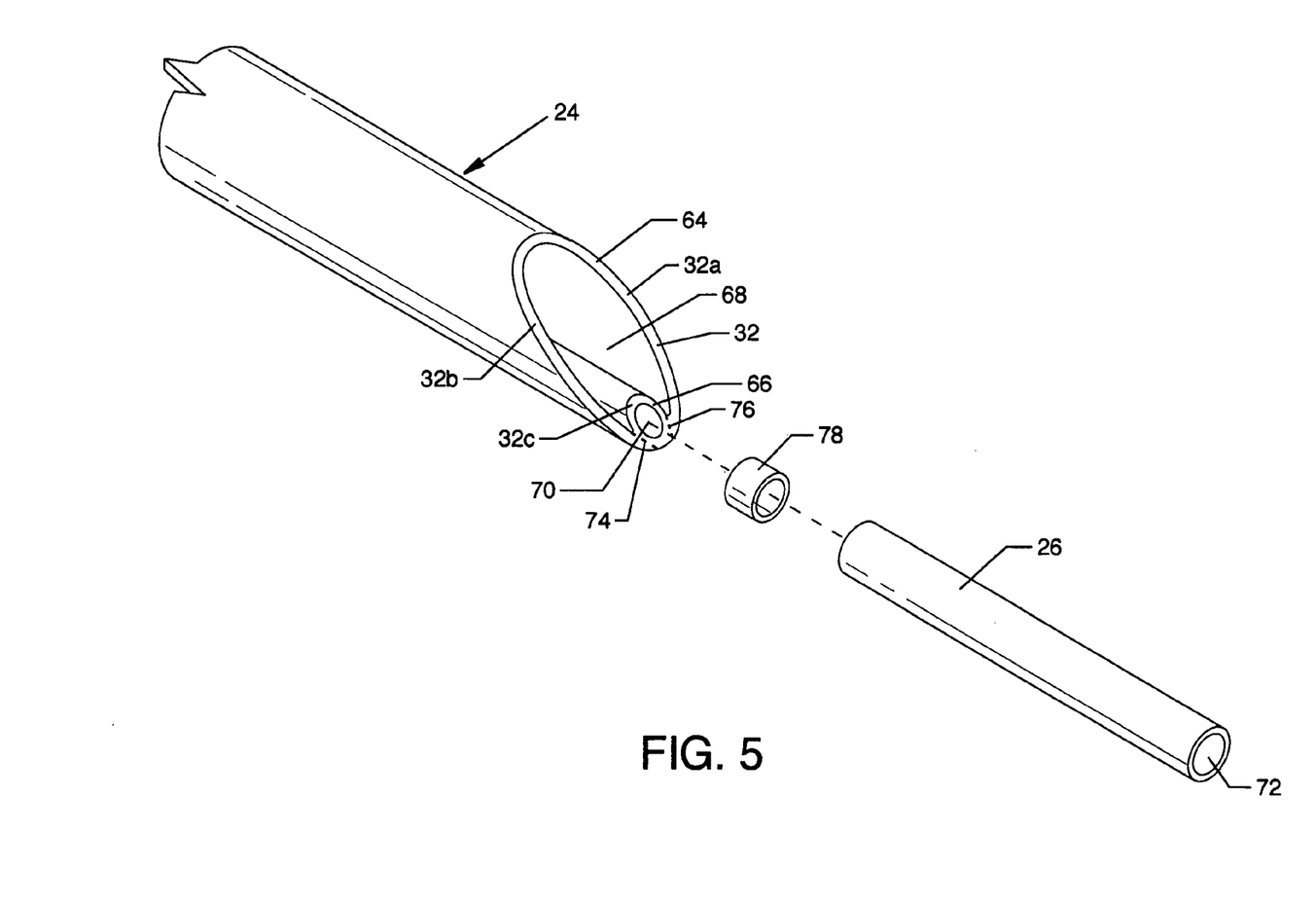
FIG. 5 is an exploded isometric view of the distal end of the dual lumen tube and associated components combined later into use therewith.
Figure 8:
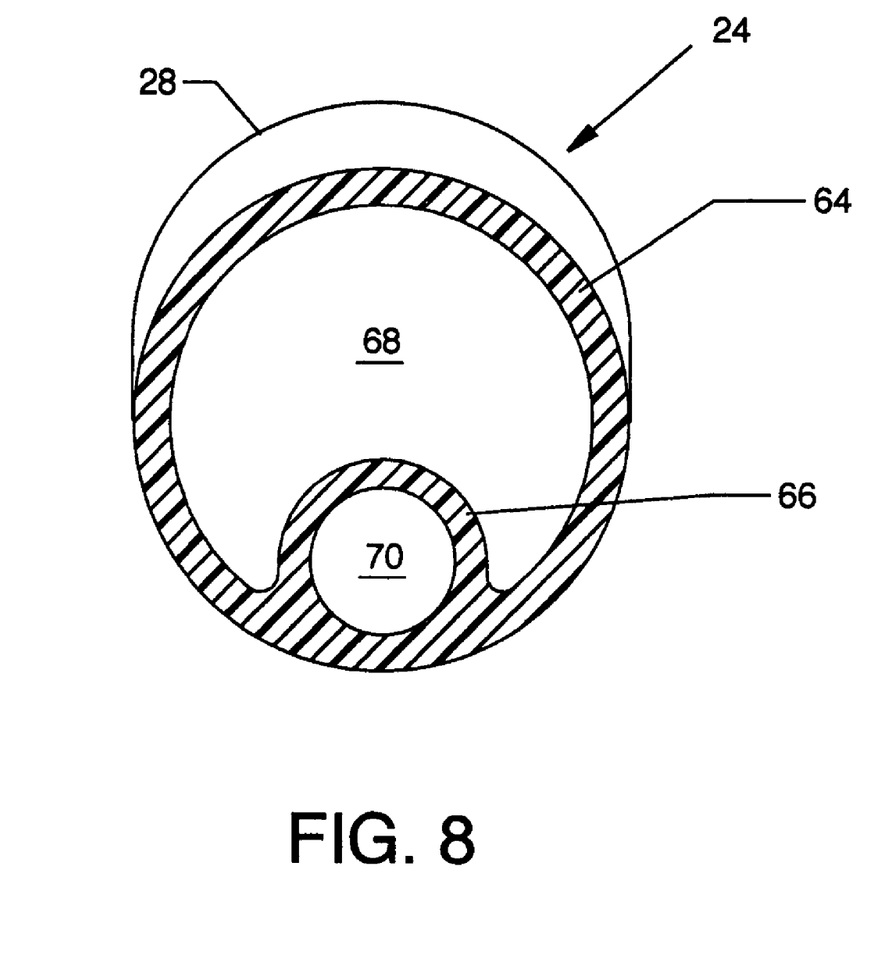
FIG. 8 is a cross section view of the dual lumen tube along line 8-8 of FIG. 7.

FIG. 5 is an exploded isometric view of the distal end of the dual lumen tube 24 and associated components combined later into use therewith. The dual lumen tube 24, preferably an extruded structure, includes a large radius tubular portion 64 and an intersecting small radius tubular portion 66. The tubular portions 64 and 66 are commonly and eccentrically co-located, thereby delineating a large lumen 68 and a small lumen 70, respectively. The small radius tubular portion 66 forms the small lumen 70 which is circular in shape. The wall of the large radius tubular portion 64 intersects the wall of the small radius tubular portion 66 to have structure in common where the combination of a greater portion of the interior surface of the large radius tubular portion 64 and a greater portion of the exterior surface of the small radius tubular portion 66 forms the structure delineating the large lumen 68. The large radius tubular portion 64 and the small radius tubular portion 66 are truncated at the distal end of each. The cross section size of the large lumen 68 is the difference between the inner surface of the large radius tubular portion 64 and the outer surface of the small radius tubular portion 66. The small lumen 70 is eccentric to and located substantially within the general profile of the large lumen 68. A cross section view of the dual lumen tube 24 is shown in FIG. 8. The distal end portion of the dual lumen tube 24, specifically the large radius tubular portion 64, includes the convex beveled edge 32 for facilitating ease of passage along a blood vessel, vein or the like having a tortuous path. The flexible tip tube 26, which includes a lumen 72, secures over and about the small radius tubular portion 66 at the distal portion of the dual lumen tube 24 at a position adjacent to and partially encompassed by the convex beveled edge 32 to communicate with the small lumen 70 of the small radius tubular portion 66. Longitudinally oriented slits 74 and 76 are made between the outer surface of the small radius tubular portion 66 and the inner surface of the large radius tubular portion 64 in order to accommodate a radiopaque marker band 78 and the flexible tip tube 26 over and about the small radius tubular portion 66.

Figure 6:
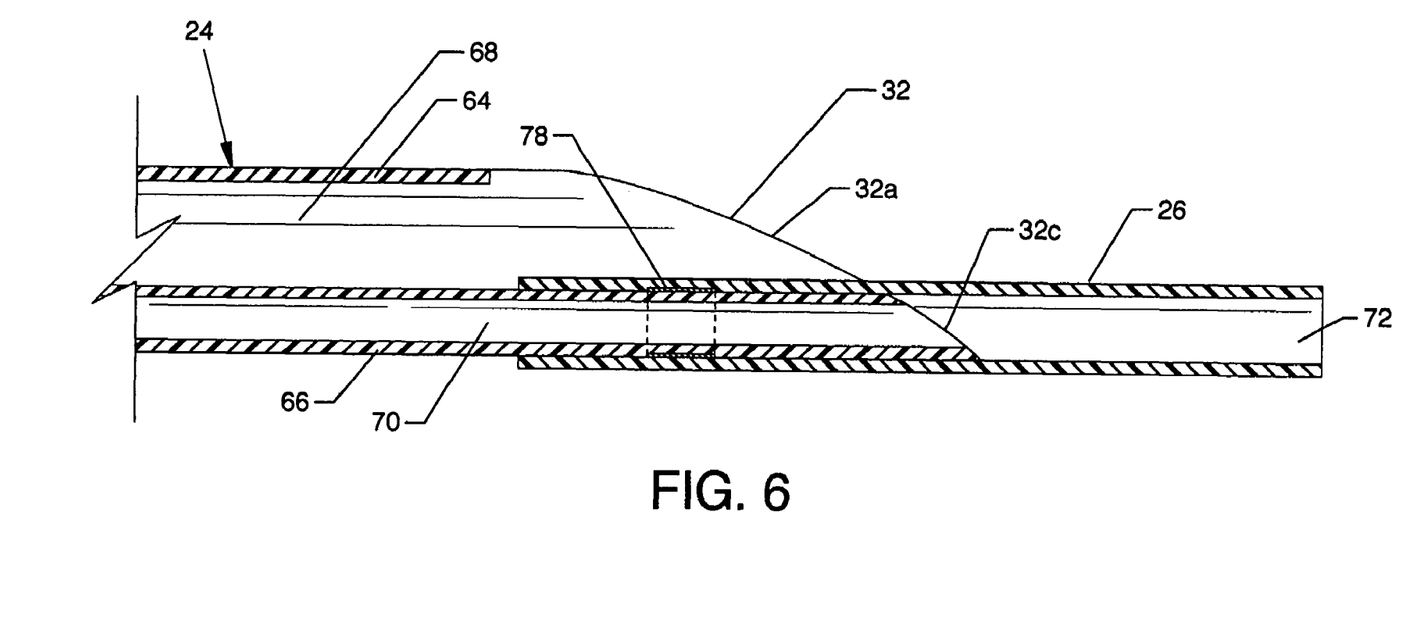
FIG. 6 is a cross section view of the dual lumen tube distal end along line 6-6 of FIG. 1.

FIG. 6 is a cross section view along line 6-6 of FIG. 1 showing the relationship of the flexible tip tube 26 and the radiopaque marker band 78 to the distal portion of the small radius tubular portion 66. The radiopaque marker band 78 aligns and secures over and about the small radius tubular portion 66. The flexible tip tube 26 aligns and secures over and about both the radiopaque marker band 78 and the distal portion of the small radius tubular portion 66, thereby providing communication of the lumen 72 of the flexible tip tube 26 with the small lumen 70 of the small radius tubular portion 66, thus forming a convenient conduit for the passage of a guidewire therethrough. Also shown is the profile of the convex beveled edge 32 of the large radius tubular portion 64 at the distal end of the dual lumen tube 24. The convex beveled edge 32 includes convex beveled edge portions 32a and 32b (FIG. 5) located to either side of an imaginary plane extending vertically along and through the longitudinal axis of the dual lumen tube 24. The extreme distal end of the small radius tubular portion 66 preferably includes a convex beveled edge portion 32c preferably complying with and being equal to the curvature, i.e, the radius of the bevel of the convex beveled edge portions 32a and 32b of the convex beveled edge 32. The convex beveled edge portions 32a and 32b of the dual lumen tube 24 promote minimum trauma passage of the distal tip of the dual lumen tube 24 through the vasculature due to the convex structure. The convex beveled edge portion 32c of the small radius tubular portion 66 also assists in entry of a guidewire through the initial point of overlap commonality between the distal end of the small radius wall 66 and the flexible tip tube 26.

Figure 7:
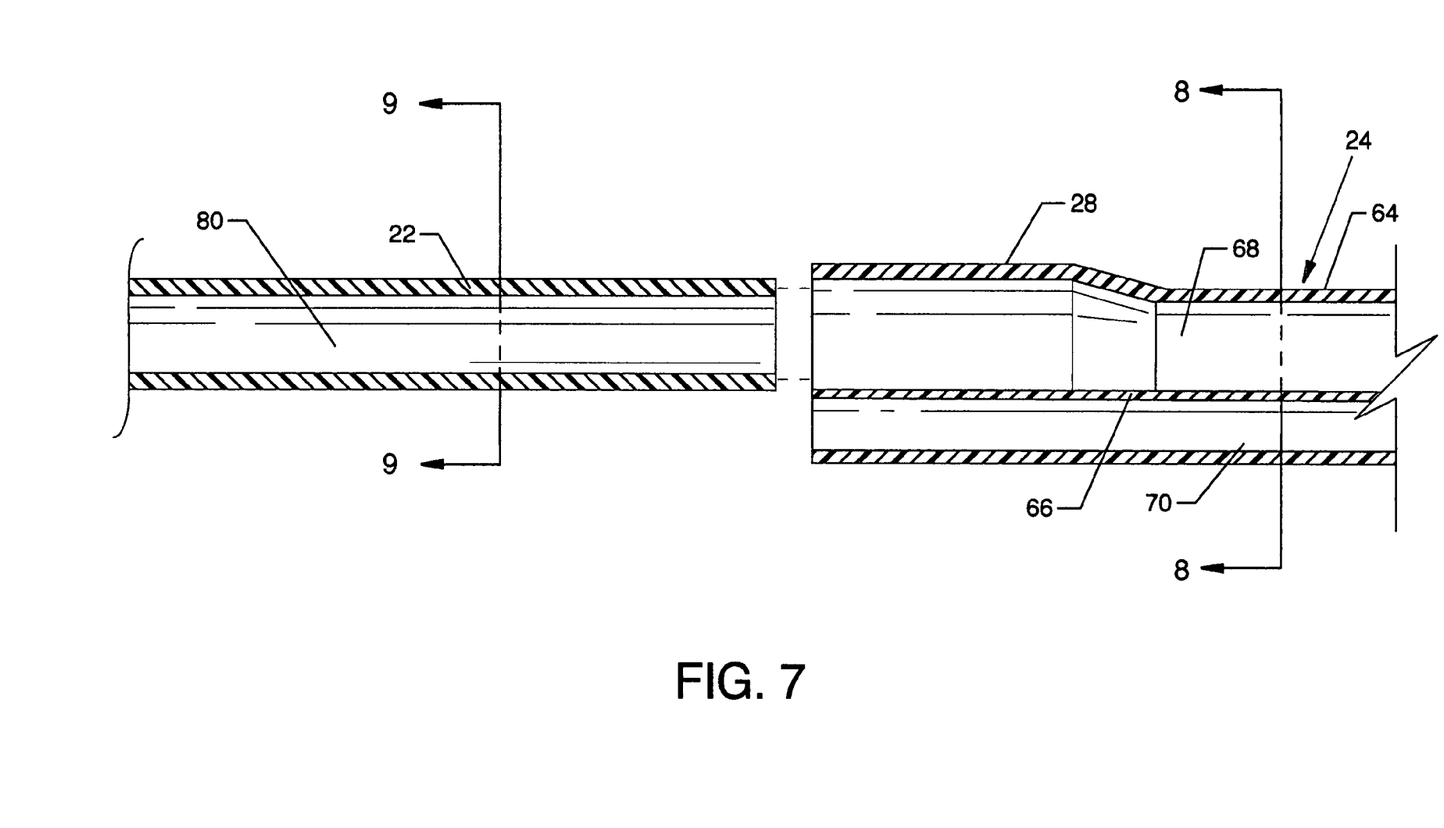
FIG. 7 is an expanded cross section view along line 7-7 of FIG. 1.

FIG. 7 is an expanded cross section view along line 7-7 of FIG. 1 showing the flared section 28 at the proximal end of the dual lumen tube 24 and the distal end of the intermediate tube 22. The flared section 28 at the proximal end of the dual lumen tube 24 accommodates the distal end of the intermediate tube 22.

FIG. 8 is a cross section view of the dual lumen tube 24 along line 8-8 of FIG. 7 showing the relationship of the small radius tubular portion 66 forming the small lumen 70 and the large radius tubular portion 64 forming the large lumen 68.

Figure 9:
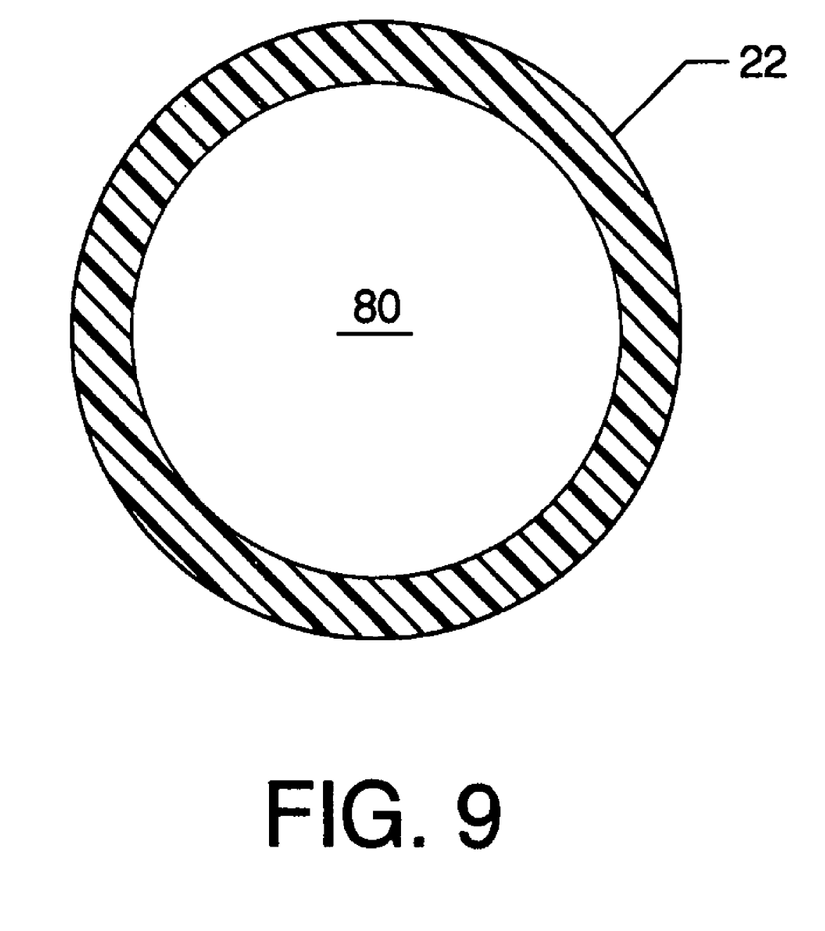
FIG. 9 is a cross section view of the intermediate tube along line 9-9 of FIG. 7.

FIG. 9 is a cross section view of the intermediate tube 22 along line 9-9 of FIG. 7.

Figure 10:
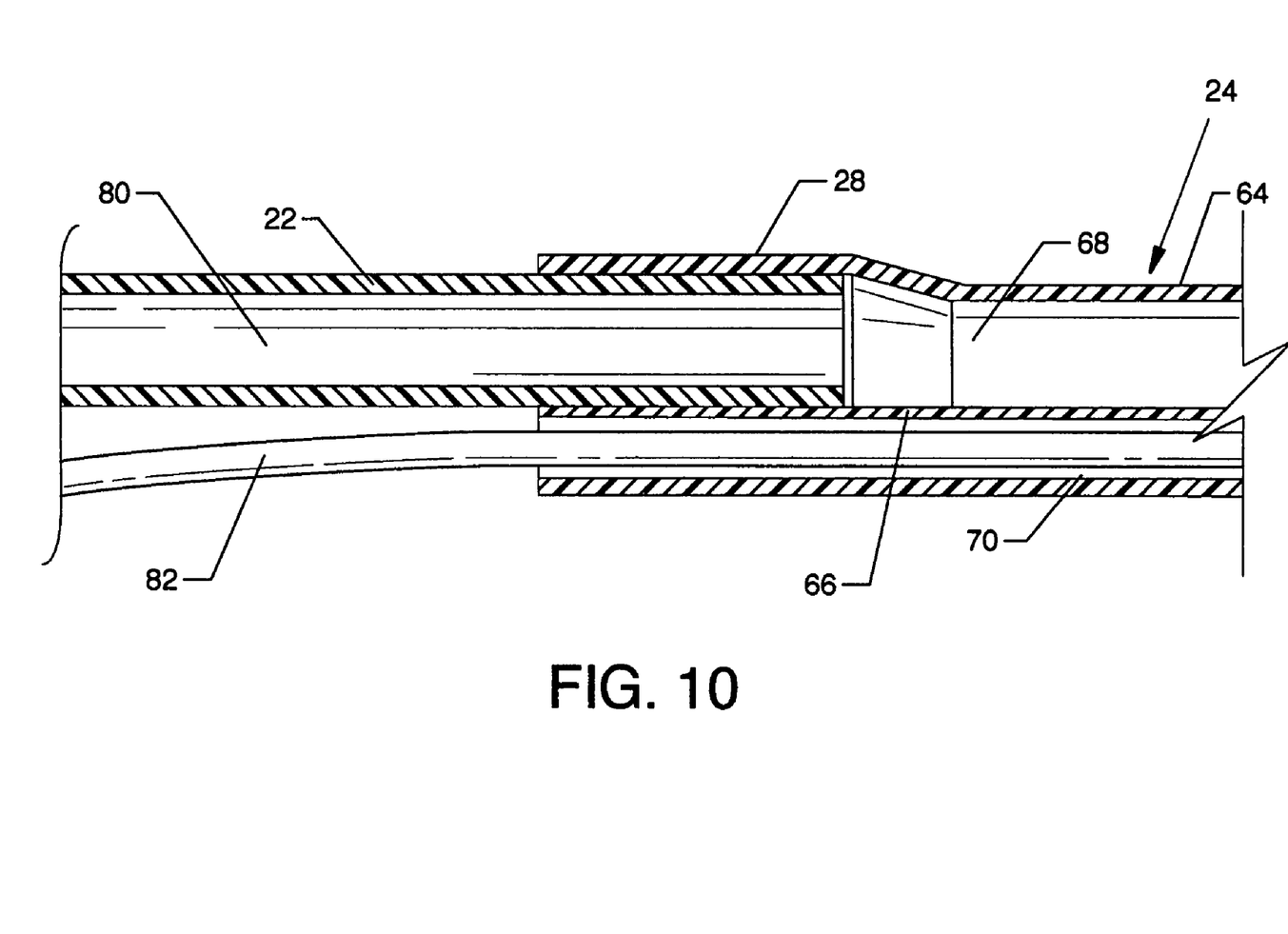
FIG. 10 is an assembled cross section view of the components of FIG. 7.

FIG. 10 is an assembled cross section view of the components of FIG. 7 where the distal end of the intermediate tube 22 is accommodated by the flared section 28 of the dual lumen tube 24. For purposes of example and illustration, a guidewire 82 is shown extending through and exiting from the small lumen 70 of the small radius tubular portion 66.

Figure 11:
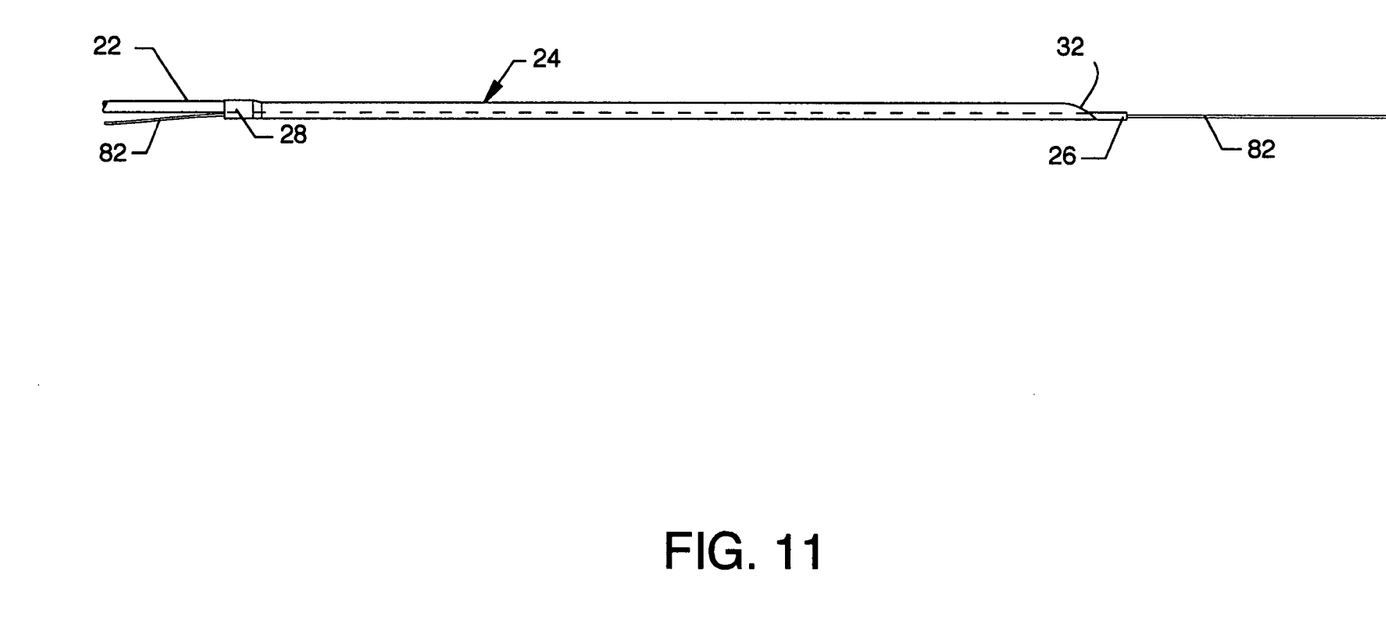
FIG. 11 shows the routing of a guidewire through the dual lumen tube.

FIG. 11 shows the routing of a guidewire 82 through the dual lumen tube 24, wherein the guidewire 82 passes through the lumen 72 of the flexible tip tube 26 and through the small lumen 70 of the small radius tubular portion 66 of the dual lumen tube 24 to exit the proximal portion thereof in close proximity to the intermediate tube 22, as shown in larger scale in FIG. 10.

Figure 12:
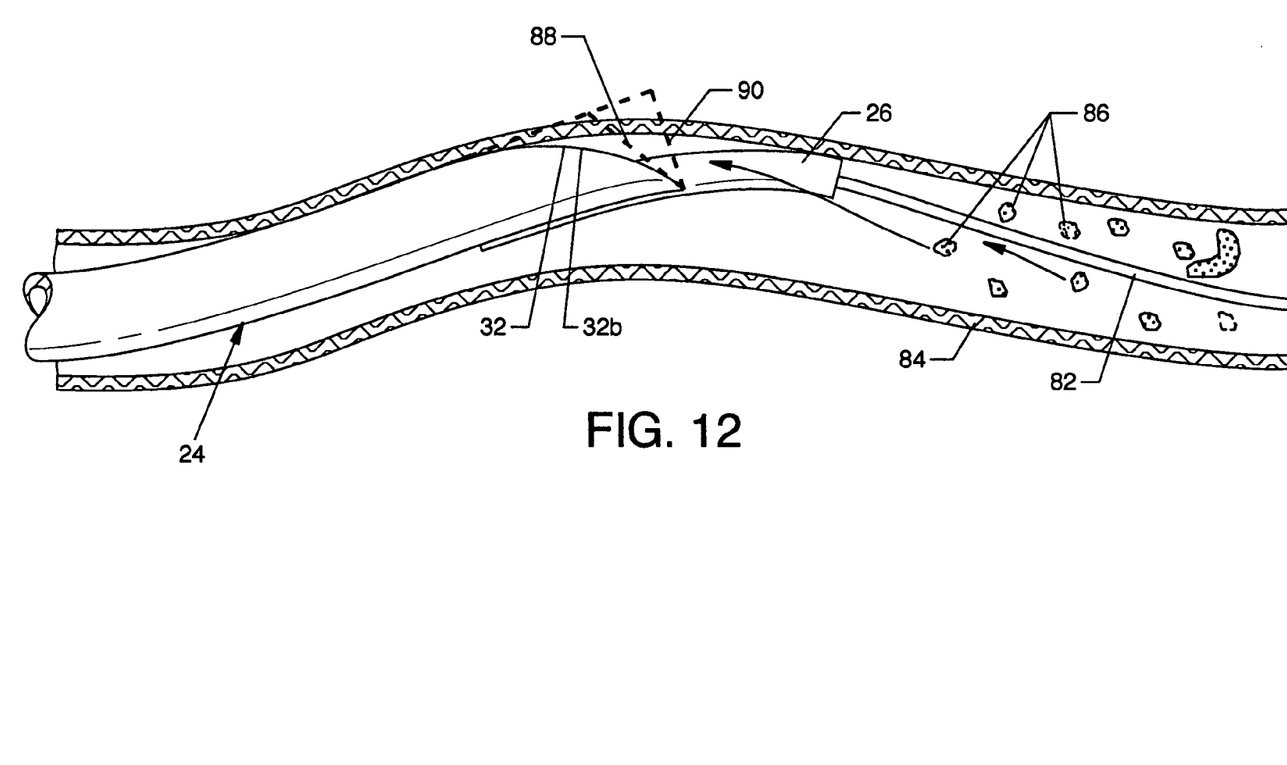

FIG. 12 shows the flexible tip tube 26 and the convex beveled edge 32 at the distal portion of the dual lumen tube 24 flexibly engaging a tortuous path along the interior of a blood vessel 84 in close proximity to the site of excess debris, thrombi, emboli and the like, such as represented by particles 86. Also shown in outline profile form is an outline of the distal ends of obtrusive prior art suction catheter devices having a simple beveled end 88 or a straight cut end 90. Such obtrusive geometry can cause contacting of the walls of the blood vessel 84 by the geometry of such devices just referenced and unfortunately can cause abrasive and traumatic impingement with the walls of the blood vessel 84.

MODE OF OPERATION

With reference specifically to FIGS. 10, 11 and 12, and to all the figures in general, the mode of operation of the present invention is now described.

A suitably sized guidewire, such as the guidewire 82, is inserted through incorporation of a conventional introducer into the vasculature, such as represented by blood vessel 84, and suitably advanced to or beyond the region of debris, thrombi, emboli and the like, such as represented by particles 86. The aspiration catheter 16 by itself or the aspiration catheter 16 with the suction assembly 18 connected thereto, along with the use of a conventional introducer, is maneuvered to cause engagement with the proximal end of the guidewire 82, whereby the proximal end of the guidewire 82 enters and is accommodated by the lumen 72 of the flexible tip tube 26, wherein the flexible tip tube 26 passes over and about the guidewire 82. The proximal end of the guidewire 82 is then accommodated by the connected small lumen 70 of the small radius tubular portion 66. The guidewire 82 is accommodated directly by the small radius tubular portion 66 of the dual lumen tube 24 and indirectly by the interior of the dual lumen tube 24 owing to the location of the small radius tubular portion 66 substantially within the large radius tubular portion 64 of the dual lumen tube 24. As the aspiration catheter 16, including the dual lumen tube 24, the intermediate tube 22, and the composite tube 20, is urged distally, the proximal end of the guidewire 82 exits the proximal end of the small radius tubular portion 66 in close proximity to the distal end of the intermediate tube 22. As the aspiration catheter 16 is urged distally along a tortuous path within the blood vessel 84 incorporating the guidance of the small radius tubular portion 66 of the dual lumen tube 24 along the guidewire 82, the soft and small profile flexible tip tube 26 gently and flexibly and with minimum trauma can contact the wall of the tortuous path blood vessel 84. The convex beveled edge portions 32a and 32b of the convex beveled edge 32 of the dual lumen tube 24 gently and with minimum trauma can contact the wall of the tortuous path blood vessel 84.

The combination of the flexible tip tube 26 and the streamlined convex beveled edge 32 of the dual lumen tube 24 provides for minimum trauma passage of the distal end of the dual lumen tube 24 through a blood vessel 84 having a tortuous path. Such association with the compact profile of the dual lumen tube 24 provides a highly flexible and maneuverable aspiration device.

The syringe 34 and the stopcock 36, as well as the other components of the suction assembly 18, are incorporated to provide controlled vacuum to the hub 12 and the aspiration catheter 16 to remove debris, thrombi, emboli and the like from a vascular site.

Various modifications can be made to the present invention without departing from the apparent scope thereof.

DUAL LUMEN ASPIRATION CATHETER SYSTEM PARTS LIST

10 dual lumen aspiration catheter system
12 hub
14 strain relief
16 aspiration catheter
18 suction assembly
20 composite tube
22 intermediate tube
24 dual lumen tube
26 flexible tip tube
28 flared section
32 convex beveled edge
32*a-c* convex beveled edge portions
34 syringe
36 stopcock
38 connector
40 extension tube
42 connector
44 tapered extension
46 main body
48 lumen
50 cavity
52 connection flange
54 orifice
56 lumen
58 tapered extension receptor
60 grasping tab
62 grasping tab
64 large radius tubular portion
66 small radius tubular portion
68 large lumen
70 small lumen
72 lumen
74 slit
76 slit
78 radiopaque marker band
80 lumen
82 guidewire
84 blood vessel
86 particle
88 simple beveled end
90 straight cut end It is claimed:

1. A dual lumen aspiration catheter system comprising:
   a. a hub and a flexible strain relief;
   b. an aspiration catheter having a proximal end and a distal end and a suction assembly which attaches to and is in communication with the aspiration catheter;
   c. said aspiration catheter including multiple successively connected flexible tubular components each increasing in relative flexibility in the distal direction, the most proximal tubular component connectingly extending from the hub and through the flexible strain relief;
   d. said tubular components of the aspiration catheter including, in order proximally to distally, a composite tube, an intermediate tube, a dual lumen tube, and a flexible tip tube, the composite tube and the intermediate tube each having a single lumen;
   e. said dual lumen tube including a large radius tubular portion and a small radius tubular portion, both said large radius tubular portion and said small radius tubular portion having a shared bottom wall, and are eccentrically co-located to delineate a large lumen and a small lumen, respectively, whereby the small lumen is eccentric to and located substantially within the general profile of the large lumen, and
   f. said dual lumen tube extending towards the distal end of the aspiration catheter such that use of both lumens occurs without interference by or of the composite tube or intermediate tube, and the distal end of the dual lumen tube having a convex beveled edge, the convex beveled edge and the flexible tip tube singly or in combination serving to facilitate ease of passage along a tortuous path of a blood vessel, vein or the like.

2. The system of claim 1, wherein said flexible tip tube secures to the small radius tubular portion at a position adjacent to and partially encompassed by the convex beveled edge to communicate with the small lumen, and said small lumen includes a proximally located exit end, whereby the flexible tip tube and the small lumen form a path for accommodation of a guidewire, and the large lumen of the large radius tubular portion is used to evacuate loose material from the blood vessel, vein or the like in cooperation with the suction assembly.

3. The system of claim 1, wherein a fluoroscopic ring or marker band is located about the distal end of the small radius tubular portion.

4. The system of claim 1, wherein the suction assembly includes a syringe, a stopcock, an extension tube, and connectors to provide for a low pressure source for evacuation of debris, thrombi, or emboli through the hub and aspiration catheter.

5. The system of claim 1, wherein the composite tube includes polyimide layers with stainless steel flat braid wires in between the polyimide layers.

6. The system of claim 4, wherein the syringe is lockable.

7. The system of claim 1, wherein the composite tube is from about 80 centimeters to about 120 centimeters in length.

8. The system of claim 1, wherein the intermediate tube is from about 15 centimeters to about 25 centimeters in length.

9. The system of claim 1, wherein the dual lumen tube is about 25 centimeters in length.

10. The system of claim 1, wherein the flexible tip tube is formed of 25-55 durometer Pebax.

11. A method of aspirating debris, thrombi, emboli or the like from a vasculature comprising the steps of:
    a. providing a dual lumen aspiration catheter including:
       (1) a hub and a flexible strain relief;
       (2) an aspiration catheter having a proximal end and a distal end and a suction assembly which attaches to and is in communication with the aspiration catheter;
       (3) said aspiration catheter including multiple successively connected flexible tubular components each increasing in relative flexibility in the distal direction, the most proximal tubular component connectingly extending from the hub and through the flexible strain relief;
       (4) said tubular components of the aspiration catheter including, in order proximally to distally, a composite tube, an intermediate tube, a dual lumen tube, and a flexible tip tube, the composite tube and the intermediate tube each having a single lumen;

(5) said dual lumen tube including a large radius tubular portion and a small radius tubular portion, both said large radius tubular portion and said small radius tubular portion have a shared bottom wall, and are eccentrically co-located to delineate a large lumen and a small lumen, respectively, whereby the small lumen is eccentric to and located substantially within the general profile of the large lumen; and (6) said dual lumen tube extending towards the distal end of the aspiration catheter such that use of both lumens occurs without interference by or of the composite tube or intermediate tube, and the distal end of the dual lumen tube having a convex beveled edge, the convex beveled edge and the flexible tip tube singly or in combination serving to facilitate ease of passage along a tortuous path of a blood vessel, vein or the like;

b. inserting a suitably sized guidewire into the vasculature, the guidewire having a proximal end and distal end, the proximal end remaining exterior to the vasculature;

c. engaging the distal end of the guidewire with the dual lumen aspiration catheter, with the guidewire initially accommodated by a lumen of the flexible tip tube and advancing the dual lumen aspiration catheter on the guidewire such that the guidewire is subsequently accommodated by the small lumen of the dual lumen tube;

d. urging the dual lumen aspiration catheter distally on the guidewire and into the vasculature; and e. applying suction to provide controlled vacuum so as to remove debris, thrombi, emboli and the like from the vasculature.

* * * * *